March 5, 1974 F. M. CRITES Plant Pat. 3,505
APPLE TREE
Filed May 30, 1972
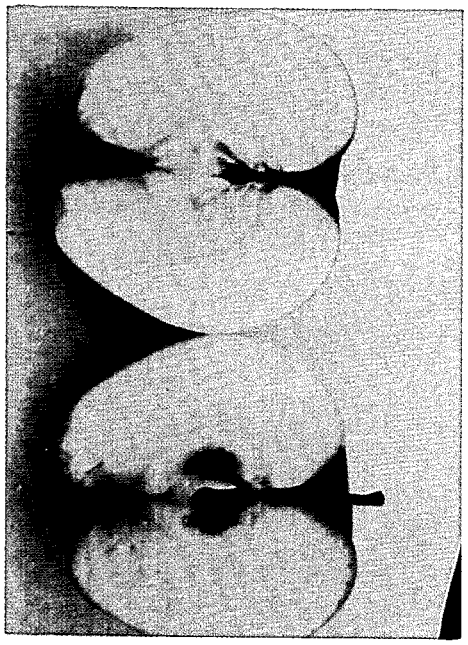
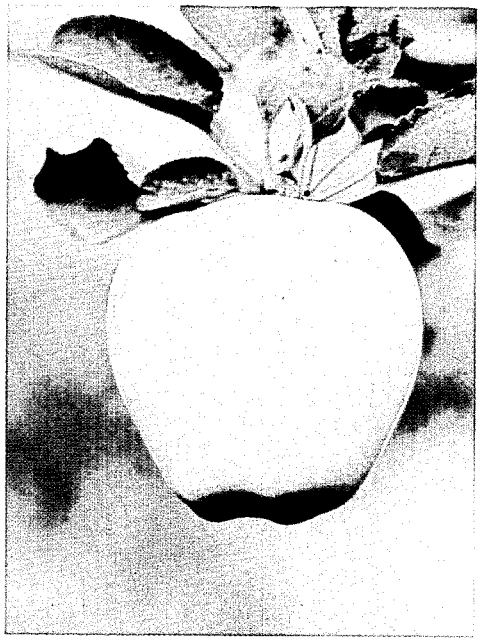
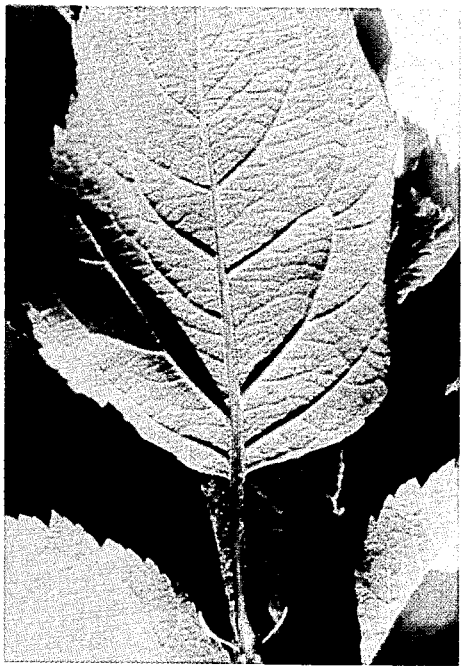
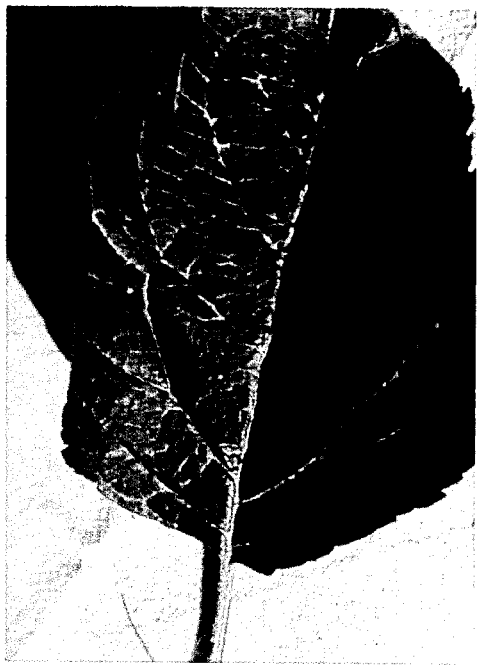

United States Patent Office

Plant Pat. 3,505
Patented Mar. 5, 1974

3,505
APPLE TREE

Francis M. Crites, Wapato, Wash., assignor to Carlton Nursery Company Inc., Dayton, Oreg.

Filed May 30, 1972, Ser. No. 257,550
Int. Cl. A01h 5/03
U.S. Cl. Plt.—34 1 Claim This invention relates to a new and distinct variety of apple tree which was discovered as a whole tree chance seedling. This discovery was made in an orchard which was being cultivated and maintained as a part of an operating fruit ranch near Wapato, Wash. This ranch was owned and managed by applicant at the time the discovery was made.

Applicant's attention was attracted to the new seedling apple tree by its glossy, golden, waxy fruits and their superior flavor and eating qualities. Immediate steps were taken to test the selection further and to preserve the seedling tree. Scions of the new clone were placed (topworked) onto other apple trees in an orchard located at Parker, Washington. Continued observations of the original seedling tree and the progency thereof which were derived by topworking the selection onto other apple trees; and of fruit storage tests conducted in my apple storage facilities using both first and second generation fruits, convinced me that its golden-yellow color, glossy-waxy appearance, firm flesh and aromatic flavor and, particularly, its excellent keeping ability in storage were of sufficient merit to justify naming the selection, securing a patent and look forward to producing trees for sale. All of the above-mentioned best fruit characteristics of the new seedling tree seemed firmly established in fruits originating from second generation growth and other succeeding propagations.

The rich distinct flavor of this new variety and its elongated, uniformly ribbed appearance and round-conic shape are somewhat similar to the "Delicious" and/or "Red Delicious" varieties of apple, which types are grown in many of the apple producing areas of the world. Its golden-waxy finish and tendency toward oiliness of skin after prolonged storage make it distinct from all other apple varieties known to us. The skin is of medium thickness and tough which is found to resist bruising during normal handling operations of the fruit.

Preliminary processing tests indicate that the new variety could become a dual purpose type apple equally good for dessert and culinary use.

The seedling tree, when discovered, was of sufficient age and size to determine its growth characteristics. The tree is of standard size and growth (non-spur type), spreading by nature and of good vigor. Several years of observation have shown it to be productive and hardy.

The accompanying photographs show typical specimens of the fruit and foliage of the new variety with the fruit shown in full color as it appears on the tree at picking date. The leaf specimens illustrate both the upper and under surfaces thereof and particularly show the characteristic pinkish-red color of the midrib and veins. Stem specimens are also shown which illustrate the numerous and large cream colored lenticils present thereon.

Th following is a detailed description of the new variety, with color terms of ordinary dictionary significance.

Parentage: Chance seedling.

Locality where observations were made: Wapato, Parker and Prosser, Wash.

Dates of first and last pickings: About October 5 and October 15, respectively.

Tree: Medium to large size; vigorous; spreading; medium dense; vase formed; rapid grower; hardy; productive; regular bearer ;non-spur type growth.

*Trunk.*—Medium stockiness; medium smooth.

*Branches.*—Medium thickness; medium smoothness; much branched. Color—light gray. Lenticels—numerous; large; cream colored.

*Leaves.*—Stipulate; pinnately veined; medium size; oval; pointed; moderately thick and ridged; rugose. Length—from 1½ inches to 1¾ inches. Color—medium dark-green. Margin — slightly crenate. Leaf-blade plane—waved and folded. Petiole—pubescent; medium length; medium thickness; broad angle with stem; pinkish-red in color almost to apex of leaf. Veins—underside pinkish-red in color.

*Flowers.*—Dates of first and full bloom—about Apr. 15 and Apr. 28, respectively. Size—large. Color—light pink. Styles—shorter than stamens.

Fruit: Maturity when described—Eating hard ripe; about Oct. 10.

*Size.*—Uniform. Axial diameter—from 3 inches to 3¼ inches. Transverse diameter—from 3 inches to 3¼ inches.

*Form.*—Irregular; ribbed. Longitudinal section—round; conic; irregular. Transverse section—angular; irregular; unequal sides.

*Cavity.*—Deep; irregular; acute. Depth—from ⅝ inch to ⅞ inch. Breadth.—from ¾ inch to 1 inch. Sides—ribbed; angular. Marking—slight russeting. Color—green to yellow.

*Basin.*—Irregular; five crowned; ribbed. Depth—⅜ inch. Breadth—1 inch.

*Stem.*—Medium long; medium stoutness. Length—¾ inch to 1 inch. Bracts—present; 2 in number.

*Calyx.*—Partly open; persistent.

*Calyx lobes.*—Erect; reflexed; separated at base. Inner surface—pubescent. Outer surface—pubescent.

*Skin.*—Medium thickness; tough, smooth; glossy; waxy; becoming very oily and/or waxy in storage. Dots—conspicuous; few;– medium size; circular; color — gray; distribution — more numerous on basal than apical end. Ground color—bright yellow at maturity. Color markings—pink blush on one cheek. Bloom—wanting. Scarfskin—wanting. General color effect—overall bright yellow, prevailing with pink blush on one cheek, which colors closely approximate those of standard Golden Delicious.

*Flesh.*—Juicy. Color—cream with yellowish tint. Texture.—firm; fine; crisp. Flavor.—mildy sweet; rich. Aroma—fragrant. Quality—best; dessert type.

*Core.*—Median. Bundle area (longitudinal section)—medium large; conic; irregular; alternate with cell. Halves of area—unequal; bundles—inconspicuous; color — green. Alternate bundles — converge at stamens. Carpels—abaxile; smooth; mucronate; unsymmetrical. Length — ¾ inch. Breadth — ⅜ inch. Cross section—broadly ovate. Length—5/16 inch. Breadth—3/16. Cell walls—thin; tough.

*Core cavity.*—Smooth.

*Core lines.*—Clasping.

*Calyx tube.*—Funnel shaped; smooth; long. Length of funnel.—⅜ inch. Width of funnel—2/16 inch. Entire depth of funnel—½ inch.

*Styles.*—Distinct; pubescent; shorter than stamens.

*Stamens.*—Median; one distinct whorl.

*Auxiliary cavity.*—Wanting.

*Sepals.*—Erect; convergent.

*Seeds.*—Three per carpel; perfect; small; plump. Color — dark brown. Point of seed — acute. Length—¼ inch. Breadth—⅛ inch.

Use: Dessert; culinary.

Keeping quality: Very good; up to six months in ordinary storage. Year-round in controlled atmosphere storage.

Resistance to insects and diseases: Medium resistance to usual insects and diseases to which apple varieties are normally subject. In orchard where found, about equal to the "Delicious" variety of apple.

General observations and comparison: The following distinctions between our new variety and the most commonly grown yellow apple, the "Golden Delicious" variety are clearly notable.

*Vegetative characteristics (leaf and shoot).*—New bark—darker, more brownish in color than in "Golden Delicious." Lenticels—slightly smaller, cream color, while those of "Golden Delicious" art more whitish in color.

*Leaves.*—Very distinct pinkish-red color of midrib and larger veins while those of "Golden Delicious" are green or only slightly pink colored.

*Fruit characteristics.*—Longer and more ribbed than fruit of "Golden Delicious." Points more conspicuous and flesh more firm and much less susceptible to bruising. Skin is tougher than skin of "Golden Delicious." More tendency toward pink blush on one cheek than the "Golden Delicious" variety. Keeping quality—Much better than "Golden Delicious" in common and/or controlled atmosphere storage; becomes very oily in storage and will not wrinkle with prolonged storage as does the "Golden Delicious" variety.

*Harvest date.*—About two weeks after "Golden Delicious" in the area where discovered.

Having thus disclosed my invention, I claim:

1. A new and distinct variety of apple tree, substantially as shown and described, characterized particularly by its smooth golden, glossy, waxy appearance at maturity and its tendency toward oiliness and excellent keeping qualities in storage, also characterized by its rich, crisp, sweet and aromatic flavor and excellent dessert and culinary qualities.

No references cited.

ROBERT E. BAGWILL, Primary Examiner